United States Patent
OuYang et al.

(10) Patent No.: US 11,980,342 B2
(45) Date of Patent: May 14, 2024

(54) MINIMALLY INVASIVE ENDOSCOPE

(71) Applicant: Micron Vision Corp., Bellevue, WA (US)

(72) Inventors: Xiaolong OuYang, Bellevue, WA (US); Shih-Ping Wang, Los Altos, CA (US)

(73) Assignee: MicronVision Corp., Bellevue, WA (US)

( * ) Notice: Subject to any disclaimer, the term of this patent is extended or adjusted under 35 U.S.C. 154(b) by 0 days.

(21) Appl. No.: 17/521,397

(22) Filed: Nov. 8, 2021

(65) Prior Publication Data

US 2022/0142460 A1    May 12, 2022

Related U.S. Application Data

(60) Provisional application No. 63/138,528, filed on Jan. 18, 2021, provisional application No. 63/128,105, (Continued)

(51) Int. Cl.
*A61B 1/00* (2006.01)
*A61B 1/05* (2006.01)
(Continued)

(52) U.S. Cl.
CPC ...... *A61B 1/00103* (2013.01); *A61B 1/00009* (2013.01); *A61B 1/00016* (2013.01);
(Continued)

(58) Field of Classification Search
CPC ............ A61B 1/00103; A61B 1/00135; A61B 1/00137; A61B 1/00144; A61B 1/00142; A61B 46/10; A61B 1/00009; A61B 1/00016; A61B 1/00045; A61B 1/00087; A61B 1/00124; A61B 1/05; A61B 1/0684; A61B 1/128; A61B 1/00105
See application file for complete search history.

(56) References Cited

U.S. PATENT DOCUMENTS

| | | | |
|---|---|---|---|
| 4,854,302 | A | 8/1989 | Allred, III |
| 4,979,497 | A | 12/1990 | Matsura |

(Continued)

FOREIGN PATENT DOCUMENTS

| | | |
|---|---|---|
| CN | 102858275 | 1/2013 |
| EP | 1690512 | 8/2006 |

(Continued)

OTHER PUBLICATIONS

International Search Report and Written Opinion of PCT/US2016/18670, dated Jul. 12, 2016.
(Continued)

*Primary Examiner* — Timothy J Neal
(74) *Attorney, Agent, or Firm* — Wissing Miller LLP

(57) ABSTRACT

An endoscope in which a reusable part is inserted into a sheath of a single-use portion that includes a needle with an imaging module at its tip and a part of the reusable portion that is not covered by the sheath is covered with a flexible cap that initially was sterile and covered the open end of the sheath, whereby the entire reusable portion is covered and sealed from the environment by the cap and the sheath during a medical procedure.

18 Claims, 10 Drawing Sheets

Related U.S. Application Data filed on Dec. 20, 2020, provisional application No. 63/118,617, filed on Nov. 25, 2020, provisional application No. 63/113,960, filed on Nov. 15, 2020, provisional application No. 63/112,739, filed on Nov. 12, 2020.

(51) Int. Cl.
  *A61B 1/06* (2006.01)
  *A61B 1/12* (2006.01)

(52) U.S. Cl.
  CPC ...... *A61B 1/00045* (2013.01); *A61B 1/00087* (2013.01); *A61B 1/00124* (2013.01); *A61B 1/00135* (2013.01); *A61B 1/00137* (2013.01); *A61B 1/00144* (2013.01); *A61B 1/05* (2013.01); *A61B 1/0684* (2013.01); *A61B 1/128* (2013.01)

(56) References Cited

U.S. PATENT DOCUMENTS

| | | |
|---|---|---|
| 5,010,876 A | 4/1991 | Henley |
| 5,188,093 A | 2/1993 | Lafferty |
| 5,281,214 A | 1/1994 | Wilkins |
| 5,323,767 A | 6/1994 | Lafferty |
| 5,329,936 A | 7/1994 | Lafferty |
| 5,486,155 A | 1/1996 | Muller |
| 5,549,547 A | 8/1996 | Cohen |
| 5,569,163 A | 10/1996 | Francis |
| 5,632,717 A | 5/1997 | Yoon |
| 5,666,561 A | 9/1997 | Stephenson |
| 5,667,472 A | 9/1997 | Finn |
| 5,667,476 A | 9/1997 | Frassica et al. |
| 5,785,644 A | 7/1998 | Grabover |
| 5,860,953 A | 1/1999 | Snoke |
| 5,873,814 A | 2/1999 | Adair |
| 5,928,137 A | 7/1999 | Green |
| 5,935,141 A | 8/1999 | Weldon |
| 5,957,947 A | 9/1999 | Wattiez |
| 6,004,264 A | 12/1999 | Sano |
| 6,007,531 A | 12/1999 | Snoke |
| 6,007,546 A | 12/1999 | Snow |
| 6,017,322 A | 1/2000 | Snoke |
| 6,033,378 A | 3/2000 | Lundquist |
| 6,059,719 A | 5/2000 | Yamamato et al. |
| 6,095,970 A | 8/2000 | Hidaka |
| 6,165,123 A | 12/2000 | Thompson |
| 6,174,307 B1 | 1/2001 | Daniel |
| 6,210,416 B1 | 4/2001 | Chu |
| 6,211,904 B1 | 4/2001 | Adair |
| 6,221,007 B1 | 4/2001 | Green |
| 6,221,070 B1 | 4/2001 | Tu et al. |
| 6,261,226 B1 | 7/2001 | McKenna |
| 6,280,386 B1 | 8/2001 | Alfano |
| 6,331,174 B1 | 12/2001 | Reinhard |
| 6,387,043 B1 | 5/2002 | Yoon |
| 6,398,743 B1 | 6/2002 | Halseth |
| 6,507,699 B2 | 1/2003 | Lemoine |
| 6,518,823 B1 | 2/2003 | Kawai |
| 6,793,882 B1 | 9/2004 | Verschuur |
| 6,917,380 B1 | 7/2005 | Tay |
| 7,256,446 B2 | 8/2007 | Hu |
| 7,428,378 B1 | 9/2008 | Warpakowski |
| 7,507,205 B2 | 3/2009 | Borovsky |
| 7,591,799 B2 | 9/2009 | Selkee |
| 7,606,609 B2 | 10/2009 | Muranushi |
| 7,780,650 B2 | 8/2010 | Frassica |
| 7,798,995 B2 | 9/2010 | Yue |
| 7,931,616 B2 | 4/2011 | Selkee |
| 7,946,981 B1 | 5/2011 | Cubb |
| 8,057,464 B2 | 9/2011 | Chen |
| 8,052,609 B2 | 11/2011 | Harhen |
| 8,187,171 B2 | 5/2012 | Irion |
| 8,197,398 B2 | 6/2012 | Scholly |
| 8,235,975 B2 | 8/2012 | Chen |
| 8,361,775 B2 | 4/2013 | Flower |
| 8,460,182 B2 | 6/2013 | Ouyang |
| 8,523,808 B2 | 9/2013 | Selkee |
| 8,696,552 B2 | 4/2014 | Whitman |
| 8,803,960 B2 | 8/2014 | Sonnenschein |
| 8,834,357 B2 | 9/2014 | Oskin |
| 8,845,522 B2 | 9/2014 | McIntyre |
| 8,952,312 B2 | 2/2015 | Blanquart |
| 8,998,844 B2 | 4/2015 | Reed |
| 9,473,749 B2 | 10/2016 | Selby |
| 9,649,014 B2 | 5/2017 | Ouyang |
| 9,736,342 B2 | 8/2017 | Mueckl |
| 9,895,048 B2 | 2/2018 | Ouyang |
| 10,278,563 B2 | 5/2019 | Ouyang |
| 10,292,571 B2 | 5/2019 | Ouyang |
| 10,595,710 B2 * | 3/2020 | Gill .................. A61B 1/00135 |
| 2001/0007051 A1 | 7/2001 | Nakashima |
| 2001/0049509 A1 | 12/2001 | Sekine |
| 2003/0016284 A1 | 1/2003 | Squilla |
| 2003/0023142 A1 | 1/2003 | Grabover |
| 2003/0078476 A1 | 4/2003 | Hill |
| 2003/0078502 A1 | 4/2003 | Miyaki et al. |
| 2003/0151680 A1 | 8/2003 | McDermott |
| 2003/0199735 A1 | 10/2003 | Dickopp |
| 2004/0054254 A1 | 3/2004 | Miyake |
| 2004/0054259 A1 | 3/2004 | Hasegawa |
| 2004/0138558 A1 | 7/2004 | Dunki-Jacobs |
| 2004/0162572 A1 | 8/2004 | Sauer |
| 2005/0010178 A1 | 1/2005 | Katz |
| 2005/0264687 A1 | 1/2005 | Murayama |
| 2005/0049459 A1 | 3/2005 | Hern |
| 2005/0085695 A1 | 4/2005 | Sherner |
| 2005/0154262 A1 | 7/2005 | Banik |
| 2005/0159646 A1 | 7/2005 | Nordstrom |
| 2005/0177027 A1 | 8/2005 | Hirata |
| 2005/0277874 A1 | 12/2005 | Selkee |
| 2005/0277875 A1 | 12/2005 | Selkee |
| 2006/0052710 A1 | 3/2006 | Miura |
| 2006/0063976 A1 | 3/2006 | Aizenfeld |
| 2006/0114986 A1 | 6/2006 | Knapp |
| 2006/0152601 A1 | 7/2006 | Parekh |
| 2006/0167340 A1 | 7/2006 | Peas |
| 2006/0171693 A1 | 8/2006 | Todd |
| 2006/0173245 A1 | 8/2006 | Todd |
| 2006/0259124 A1 | 11/2006 | Matsuoka |
| 2006/0287576 A1 | 12/2006 | Tsuji |
| 2007/0060789 A1 | 3/2007 | Uchimura |
| 2007/0081920 A1 | 4/2007 | Murphy |
| 2007/0117437 A1 | 5/2007 | Boehnlein |
| 2007/0129604 A1 | 6/2007 | Hatcher |
| 2007/0162095 A1 | 7/2007 | Kimmel |
| 2007/0167678 A1 | 7/2007 | Moskowitz |
| 2007/0167868 A1 | 7/2007 | Sauer |
| 2007/0173693 A1 | 7/2007 | Refael |
| 2007/0188604 A1 | 8/2007 | Miyamoto |
| 2007/0197875 A1 | 8/2007 | Osaka |
| 2007/0210162 A1 | 9/2007 | Keen |
| 2007/0225556 A1 | 9/2007 | Ortiz |
| 2007/0238927 A1 | 10/2007 | Ueno |
| 2008/0004642 A1 | 1/2008 | Birk |
| 2008/0071144 A1 | 3/2008 | Kimmel |
| 2008/0097550 A1 | 4/2008 | Dicks |
| 2008/0108869 A1 | 5/2008 | Sanders |
| 2008/0195125 A1 | 8/2008 | Orbay |
| 2008/0195128 A1 * | 8/2008 | Orbay ............ A61B 17/320036 600/183 |
| 2008/0225410 A1 | 9/2008 | Ning |
| 2008/0234547 A1 | 9/2008 | Irion et al. |
| 2008/0255416 A1 | 10/2008 | Gilboa |
| 2008/0262306 A1 | 10/2008 | Kawai |
| 2008/0300456 A1 | 12/2008 | Irion |
| 2009/0027489 A1 | 1/2009 | Takemura |
| 2009/0065565 A1 | 3/2009 | Lemoine |
| 2009/0076321 A1 | 3/2009 | Suyama |
| 2009/0076328 A1 * | 3/2009 | Root .................. A61B 1/00034 600/131 |
| 2009/0080214 A1 | 3/2009 | Watanabe |
| 2009/0105538 A1 | 4/2009 | Van Dam |

(56) References Cited

U.S. PATENT DOCUMENTS

| | | |
|---|---|---|
| 2009/0118580 A1 | 5/2009 | Sun |
| 2009/0118641 A1 | 5/2009 | Van Dam |
| 2009/0149713 A1 | 7/2009 | Niida |
| 2009/0225159 A1 | 9/2009 | Schneider |
| 2009/0227897 A1 | 9/2009 | Wendt |
| 2009/0229842 A1 | 9/2009 | Gray |
| 2009/0240245 A1 | 9/2009 | Deville |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |
| 2010/0026201 A1 | 10/2010 | Frangioni |
| 2011/0009694 A1 | 1/2011 | Schultz |
| 2011/0034769 A1 | 2/2011 | Adair |
| 2011/0037876 A1 | 2/2011 | Talbert |
| 2011/0054446 A1 | 3/2011 | Schultz |
| 2011/0092775 A1 | 4/2011 | Deshmukh |
| 2011/0105839 A1 | 5/2011 | Hoffman |
| 2011/0112622 A1 | 5/2011 | Phan |
| 2011/0130627 A1 | 6/2011 | McGrail |
| 2011/0211115 A1 | 9/2011 | Tsai |
| 2011/0213206 A1 | 9/2011 | Boutillette |
| 2011/0245602 A1 | 10/2011 | Brannon |
| 2011/0288482 A1 | 11/2011 | Farrell |
| 2012/0016191 A1 | 1/2012 | Ito |
| 2012/0040305 A1 | 2/2012 | Karazivan |
| 2012/0053515 A1 | 3/2012 | Crank |
| 2012/0100729 A1 | 4/2012 | Edidin |
| 2012/0165916 A1 | 6/2012 | Jordan |
| 2012/0178991 A1 | 7/2012 | Clark |
| 2012/0206591 A1 | 8/2012 | Selby |
| 2012/0226103 A1 | 9/2012 | Gunday |
| 2012/0236138 A1 | 9/2012 | Liu |
| 2012/0245242 A1 | 9/2012 | Peiffer |
| 2012/0245418 A1 | 9/2012 | Boulais |
| 2012/0253116 A1 | 10/2012 | Sniffin |
| 2012/0259203 A1 | 10/2012 | Devereux |
| 2012/0286020 A1 | 11/2012 | Smith |
| 2012/0289858 A1 | 11/2012 | Ouyang |
| 2013/0035553 A1 | 2/2013 | Kongstorum |
| 2013/0046142 A1* | 2/2013 | Remijan ............... A61B 1/042 |
| | | 600/109 |
| 2013/0057667 A1 | 5/2013 | McGrath |
| 2013/0150672 A1 | 6/2013 | Fujitani |
| 2013/0172676 A1 | 7/2013 | Levy |
| 2013/0225921 A1 | 8/2013 | Liu |
| 2013/0253402 A1 | 9/2013 | Badawi |
| 2013/0289559 A1 | 10/2013 | Reid |
| 2013/0324973 A1 | 12/2013 | Reed |
| 2013/0345514 A1 | 12/2013 | Manion |
| 2014/0022649 A1 | 1/2014 | Echhardt |
| 2014/0107416 A1* | 4/2014 | Birnkrant ........... A61B 1/00105 |
| | | 600/110 |
| 2014/0111634 A1 | 4/2014 | Mueckl |
| 2014/0154399 A1 | 6/2014 | Weikart |
| 2014/0180007 A1 | 6/2014 | Edidin |
| 2014/0213848 A1 | 7/2014 | Moskowitz |
| 2014/0228635 A1 | 8/2014 | Tuliakov |
| 2014/0275763 A1* | 9/2014 | King ............... A61B 1/00105 |
| | | 600/110 |
| 2014/0296866 A1 | 10/2014 | Salman |
| 2014/0323991 A1 | 10/2014 | Tang |
| 2015/0005575 A1 | 1/2015 | Kobayashi |
| 2015/0011830 A1 | 1/2015 | Hunter |
| 2015/0018622 A1 | 1/2015 | Tesar |
| 2015/0018710 A1 | 1/2015 | Furlong |
| 2015/0150441 A1 | 6/2015 | Ouyang |
| 2015/0164313 A1 | 6/2015 | Oyuang |
| 2015/0196197 A1 | 7/2015 | Kienzle |
| 2015/0238251 A1 | 8/2015 | Shikhman |
| 2015/0297311 A1 | 10/2015 | Tesar |
| 2016/0000300 A1 | 1/2016 | Williams |
| 2016/0073853 A1 | 3/2016 | Venkatesan et al. |
| 2016/0077008 A1 | 3/2016 | Takasu |
| 2016/0174819 A1 | 6/2016 | Ouyang |
| 2016/0334694 A1 | 11/2016 | Liu |
| 2016/0367119 A1 | 12/2016 | Ouyang |
| 2017/0086651 A1 | 3/2017 | Sato |
| 2017/0188793 A1 | 7/2017 | Ouyang |
| 2017/0188795 A1 | 7/2017 | Ouyang |
| 2017/0215699 A1 | 8/2017 | Ouyang |
| 2017/0295347 A1 | 10/2017 | Schneider |
| 2017/0310858 A1 | 10/2017 | Mueckl |
| 2018/0132700 A1 | 5/2018 | Ouyang |
| 2018/0184892 A1 | 7/2018 | Truckai |
| 2018/0235441 A1 | 8/2018 | Huang |
| 2018/0256009 A1 | 9/2018 | Ouyang |
| 2019/0029497 A1 | 1/2019 | Mirza |
| 2019/0142262 A1 | 5/2019 | Inglis |
| 2019/0216325 A1 | 7/2019 | Ouyang |
| 2019/0223691 A1 | 7/2019 | Takatsuji |
| 2019/0246873 A1* | 8/2019 | Lu ................ A61B 1/00078 |
| 2019/0246884 A1* | 8/2019 | Lu ................ A61B 1/00105 |
| 2019/0282071 A1 | 9/2019 | Ouyang |
| 2019/0282073 A1 | 9/2019 | Truckai |
| 2019/0320879 A1 | 10/2019 | Langell |
| 2019/0374095 A1 | 12/2019 | Lord |
| 2020/0204776 A1 | 6/2020 | Themelis |
| 2020/0214739 A1* | 7/2020 | Shi ................ A61B 90/361 |
| 2020/0221932 A1 | 7/2020 | Ouyang |
| 2020/0275827 A1* | 9/2020 | Weise ............... A61B 34/74 |
| 2020/0323555 A1 | 10/2020 | Long |
| 2021/0228806 A1* | 7/2021 | Streeter ........... A61M 5/31596 |
| 2021/0244265 A1 | 8/2021 | Chou |
| 2021/0401277 A1 | 12/2021 | Ouyang |

FOREIGN PATENT DOCUMENTS

| | | | |
|---|---|---|---|
| EP | 2560589 | 4/2010 | |
| EP | 3384879 | 4/2011 | |
| EP | 2749258 | 7/2014 | |
| EP | 3078354 | 10/2016 | |
| JP | 2009148420 | 7/2009 | |
| WO | 2011133792 | 10/2011 | |
| WO | 2012060932 | 5/2012 | |
| WO | 2014031192 | 2/2014 | |
| WO | 2014065901 | 5/2015 | |
| WO | 2016032729 | 3/2016 | |
| WO | 2016040131 | 3/2016 | |
| WO | 2016137838 | 9/2016 | |
| WO | WO-2017040692 A1 * | 3/2017 | ......... A61B 1/00071 |
| WO | 2018136950 | 7/2018 | |
| WO | WO-2018136950 A1 * | 7/2018 | ......... A61B 1/00039 |
| WO | 2019237003 | 12/2019 | |

OTHER PUBLICATIONS

International Search Report and Written Opinion of PCT/US2018/014880, dated Jun. 6, 2018.

International Search Report and Written Opinion of PCT/US2018/065396, dated Feb. 24, 2017.

International Search Report and Written Opinion of PCT/US2021/050095 dated Dec. 17, 2021.

International Search Report and Written Opinion of PCT/US2019/036060 dated Aug. 27, 2019.

International Search Report and Written Opinion of PCT/US2017/053171 dated Dec. 5, 2017.

International Preliminary Report on Patentability of PCT/US2017/053171 completed on Jul. 1, 2019.

(56) References Cited

OTHER PUBLICATIONS

Extended European Search Report of European Patent Application No. EP19816177 completed Feb. 2, 2022.

* cited by examiner

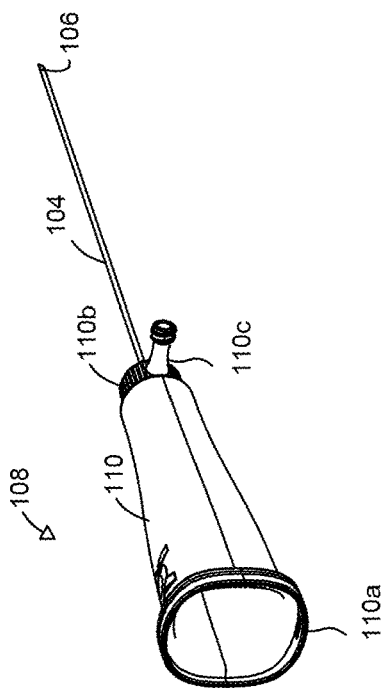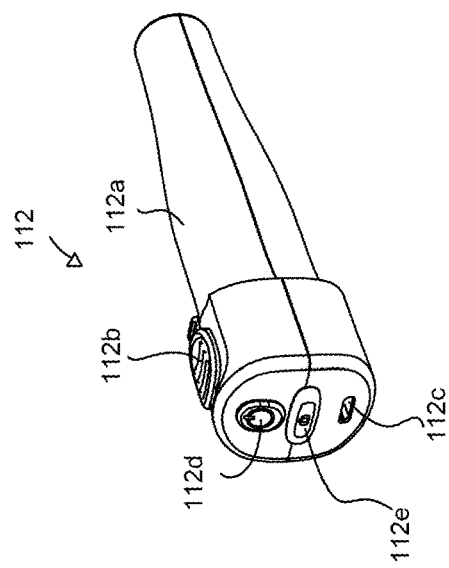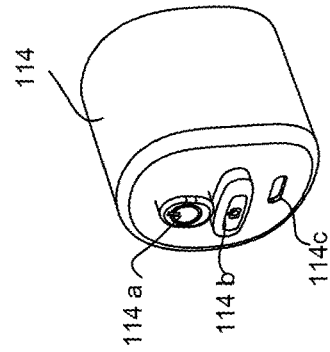
Fig.2

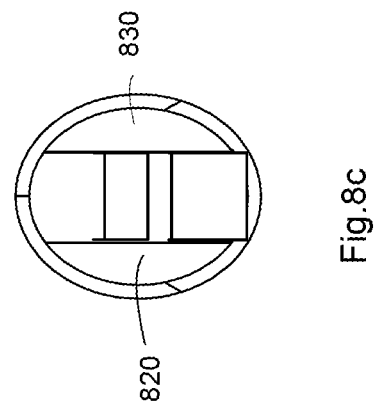
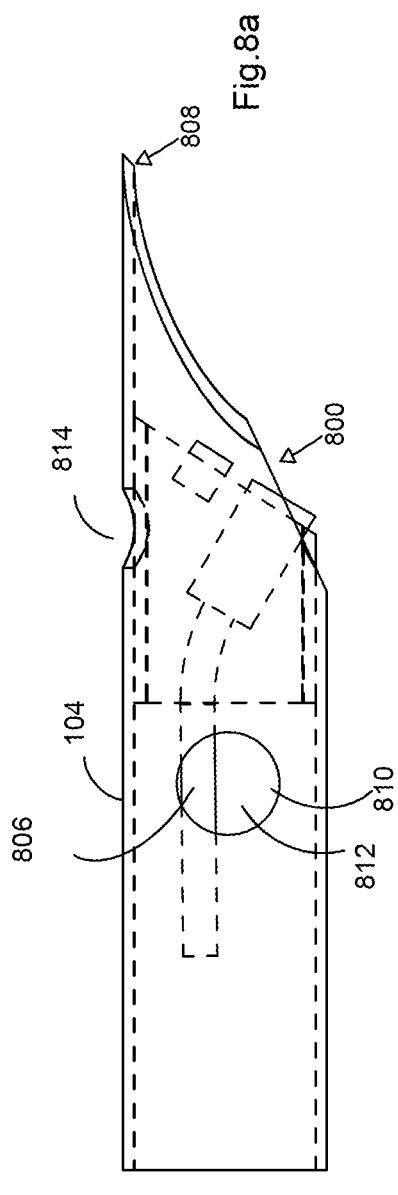
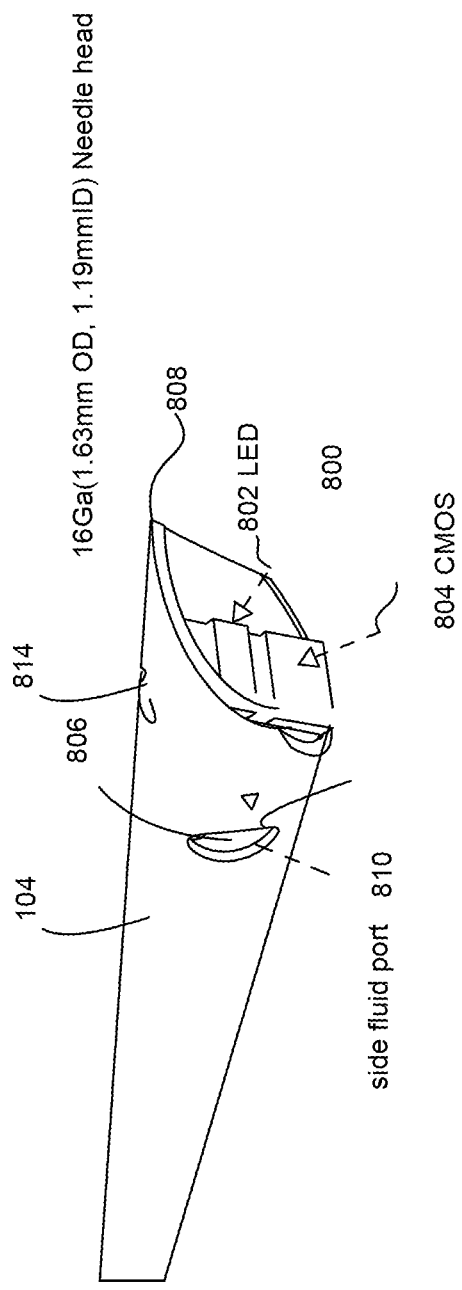

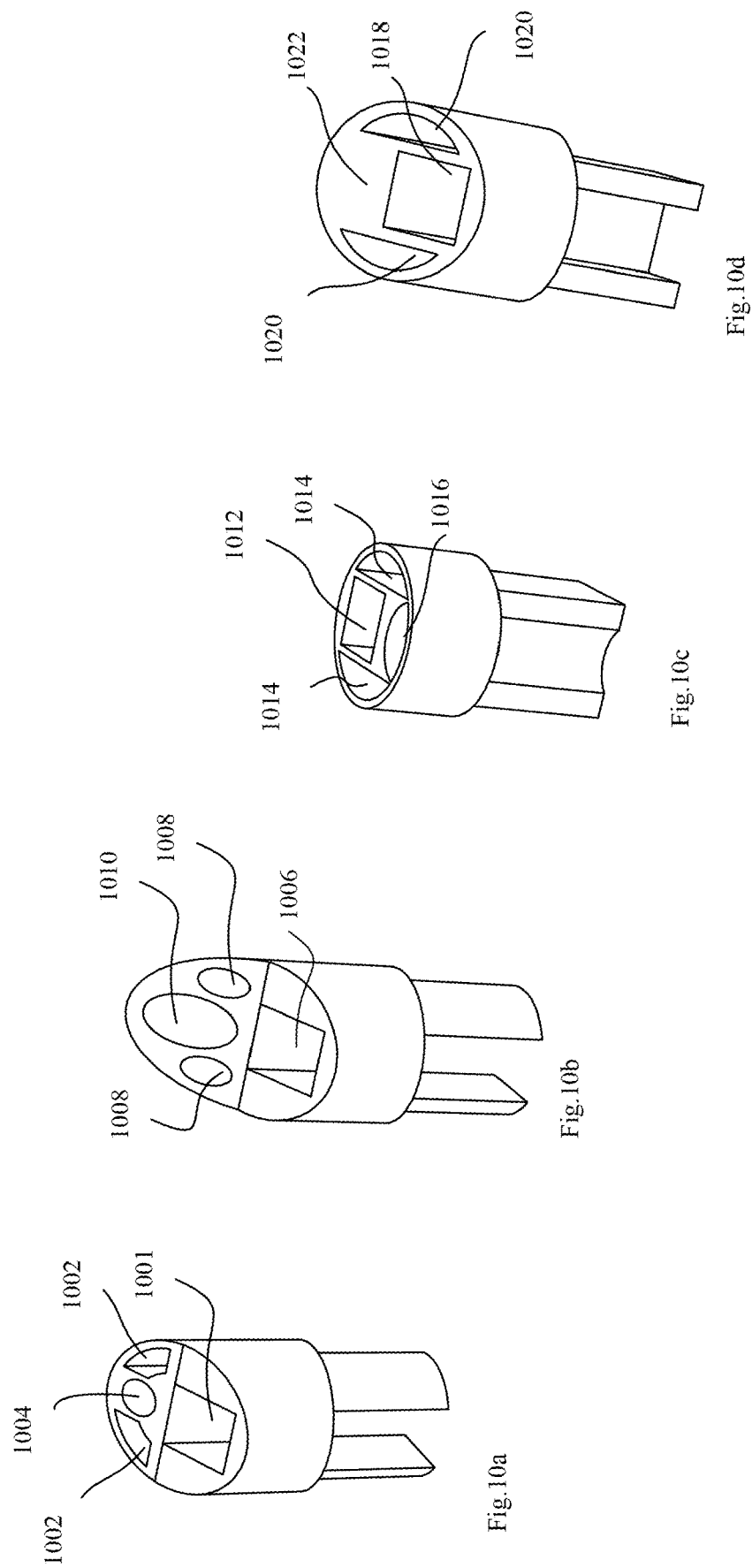

MINIMALLY INVASIVE ENDOSCOPE

REFERENCE TO RELATED APPLICATIONS

This application claims priority to and incorporates by reference each of the following U.S. Provisional Patent Application 63/112,739 filed Nov. 12, 2020; 63/113,960 filed Nov. 15, 2020; 63/118,617 filed Nov. 25, 2020; 63/128,105 filed Dec. 20, 2020; and 63/138,528 filed Jan. 18, 2021

FIELD

This patent specification relates to endoscopes and more specifically to endoscopes for medical procedures that have lower manufacturing cost and can be fully or partly disposable.

BACKGROUND

Conventional endoscopy, or direct vision used to examine the interior of a hollow organ or cavity of the body, uses a complex lens system for transmitting the image for the distal tip of the endoscope to a viewer. The lens system is typically an objective lens plus a relay lens system in the case of rigid endoscopes or a bundle of optic fibers in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

Disposable endoscopy is a more recent category of endoscopic instruments. In some cases, the manufacture of endoscopes can be made sufficiently inexpensive to be used on a single patient only. Disposable or single-use endoscopy lessens the risk of cross-contamination and hospital acquired diseases, make it possible to perform procedures in doctors' offices as well as in clinics and hospitals, and reduce the overall cost of medical procedures as they avoid expenses associated with sterilizing and maintaining traditional endoscopes and personnel needed for such maintenance.

Examples of endoscopes, including partly of fully disposable endoscopes, are discussed in the following patents and patent applications, each of which is hereby incorporated by reference: PCT/US2017/053171 filed Sep. 25, 2017; patent application U.S. Ser. No. 16/363,209 filed Sep. 25, 2017 and published as 20190216325 on Jul. 18, 2019; PCT/US2019/036060 filed Jun. 7, 2019; patent application U.S. Ser. No. 16/972,989 filed Jun. 7, 2019 and published as 20210251789 on Aug. 19, 2021; patent application U.S. Ser. No. 17/362,043 filed Jun. 29, 2021; PCT/US21/50095 filed Sep. 13, 2021; patent application U.S. Ser. No. 17/473,587 filed Sep. 13, 2021; U.S. Pat. No. 8,702,594; PCT/US16/65396 filed Dec. 7, 2016; U.S. Pat. No. 9,649,014; PCT/US2018/014880, filed Jan. 23, 2018; U.S. Pat. Nos. 10,874,287; 9,895,048; 10,524,636; 10,426,320; 10,278,563; 10,292,571; patent application U.S. Ser. No. 16/407,028 filed May 8, 2019 and published as 20190261836 on Aug. 29, 2019; PCT/US2020/038349 filed Jun. 18, 2020; PCT/US2020/046018 filed Aug. 12, 2020; U.S. Pat. Nos. 10,869,592; 11,013,396; 11,071,442; patent application U.S. Ser. No. 17,122,282 filed Dec. 15, 2020 and published as 20210093169 on Apr. 1, 2021; patent application U.S. Ser. No. 17/145,466 filed Jan. 11, 2021 and published as 20210137352 on May 13, 2021; patent application U.S. Ser. No. 17/349,674 filed Jun. 16, 2020 and published as 20210307591 on Oct. 7, 2021; and patent application U.S. Ser. No. 17/370,575 filed Jul. 8, 2021.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the accompanying drawings in which:

FIG. 2 is an exploded perspective view of an endoscope, according to some embodiments.

FIGS. 8*a* and 8*b* are a side view and a perspective view, respectively, of a distal part of an endoscope needle, according to some embodiments. FIG. 8*c* is the cross section view of the distal tip.

FIG. 10*a-d* show in perspective details of alternative distal portions of an endoscope needle, according to some embodiments.

SUMMARY OF THE DISCLOSURE

Figure 1:
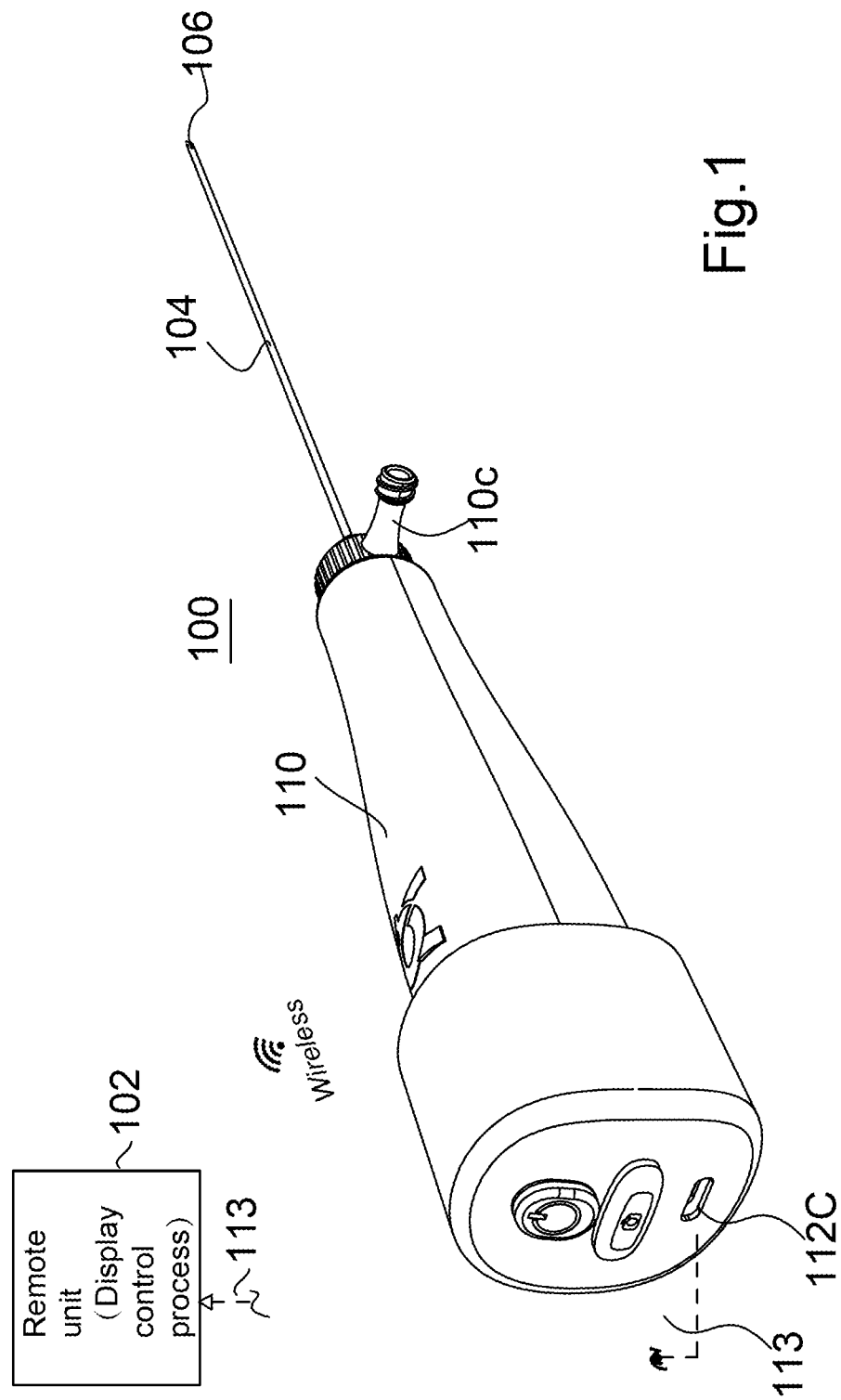
FIG. 1 is a perspective view of an endoscope and a remote unit such as a display, according to some embodiments.

According to some embodiment, an endoscope comprises: a single-use portion that comprises (a) an elongated, hollow, funnel-shaped sheath that has an open proximal end and (b) a needle that extends distally from a distal end of the sheath and has an imaging module at a distal end of the needle; a reusable portion that comprises a proximal part and an elongated distal part that is configured to fit inside said sheath through said open proximal end of the sheath; a first connector inside said sheath that is coupled with said imaging module and a second connector at said distal part of the reusable portion; wherein said connectors electrically couple to each other when the distal part of the reusable portion is in said sheath; wherein the sheath overlies a majority of the length of said reusable portion when the endoscope is assembled with the distal part of the reusable portion in the sheath and the connectors in electrical contact with each other; and electronics in said reusable portion configured to communicate with said imaging module in the needle, including for processing image data from said imaging module, and to send image data for remote display at a unit physically uncoupled from the endoscope.

The endoscope can further include one or more of the following features: (a) a sterile cap that releasably seals said open end of the sheath before the single-use and reusable portions are assembled to form the endoscope: (b) a cap that releasably covers and seals said proximal portion of the reusable portion and wherein the sheath covers the distal part of the reusable portion when the endoscope is assembled, so that the reusable portion is not exposed to the environment during a medical procedure; (c) the proximal end of the reusable portion can have one or more manually operated switches and said cap can be configured to securely fit over said one or more switches and seal them from external fluids while allowing manual operation of the one or more switches through the cap; (d) a sterile cap that releasably seals said open end of the sheath before the single-use and reusable portions are assembled to form the endoscope, wherein said cap is configured to securely fit thereafter over the proximal part of said reusable unit to seal it from external fluids; (e) the imaging module at the distal end of the needle can comprise a video sensor with a direction of view that has a central axis angled relative to a long axis of the needle and one or more LEDs configured to illuminate a field of view of said sensor; (f) the imaging module at the distal end of the needle can comprise a video sensor with a direction of view that has a central axis angled 30 degrees relative to a long axis of the needle and one or more LEDs configured to illuminate a field of view of said camera; (g) the imaging module at the distal end of the needle can comprise a video sensor with a field of view that has a central axis angled relative to a long axis of the needle, the reusable portion can include an LED-implemented light source, the single-use portion can include a light port and one or more light conductors from the light port to the distal end of the needle, and the reusable portion can include a light port coupling with the light port of the single-use portion to transmit light from the light source in the reusable portion to the distal end of the needle to illuminate a field of view of the sensor; (h) the reusable portion can include a battery, an LED light source powered with the battery, and a heat sink for the light source; (i) said single-use portion can include a first fluid port at a distal portion of the sheath, and said needle can include a second fluid port at a distal end thereof, and said single-use portion can include an internal lumen coupling said first and second ports for fluid flow; (j) said needle can have an outside diameter of 1-1.6 mm and can include a fluid lumen with an inside dimension equivalent to a diameter greater than 0.55 mm and matching 22 Ga or more; the distal end of the needle can be beveled and can have a sharp tip to facilitate puncturing and penetrating tissue; (k) said imaging module can comprise a video sensor with an imaging plane angled at 20-80 degrees to a longitudinal axis of the needle to thereby provide a central direction of view of the camera that is angled relative to said axis; (l) said reusable portion can include a transmitter configured to wirelessly transmit image data to a remote display; and (m) said reusable portion can include a port for a cable configured to transmit image date to a remote display.

According to some embodiments, a method comprises: fitting by hand a reusable portion of an endoscope in a hollow, funnel-shaped sheath of a single-use portion that has a needle extending distally from a distal end of the sheath; pushing the reusable portion distally into the sheath to make electrical contact between a connector in the reusable portion and a connector inside the sheath to thereby assemble an endoscope; carrying out a medical procedure with the assembled endoscope that includes taking images with an imaging module at a distal end of the needle and delivering image data to electronics in the reusable portion through a cable in the single use portion and said connectors; processing the image data with electronics in said reusable portion; transmitting processed image data from the reusable portion to an external unit that includes an image display; and thereafter disassembling the endoscope by pulling the reusable portion from the sheath.

The method can further include one or more of the following features: (a) a proximal part of the reusable portion can extend proximally from the sheath when the endoscope is assembled, and a cap can be placed over said proximal part of the reusable portion, whereby the entire reusable portion is covered with said sheath and said cap during a medical procedure using the endoscope; and (b) placing a sterile cap at the open end of said sheath and sealing the sheath, cap, and needle in a sterile package before using the single-use portion for a medical procedure, and thereafter removing the cap from the sheath and placing the cap over a proximal part of the reusable part to thereafter keep the entire reusable portion covered by the cap and the sheath and protected from the environment during a medical procedure.

According to some embodiments, an endoscope comprises: a single-use portion that includes a funnel-shaped sheath with an open proximal end and a needle that extends distally from a distal end of the sheath; a reusable portion a distal part of which releasably fits by hand in the sheath to assemble said endoscope with a proximal part of the reusable portion extending proximally from the sleeve; electrical connectors in the reusable portion and the sheath that make electrical contact with each other when the endoscope is assembled; said single-use portion further comprising a needle that extends distally from the sheath and has an imaging module at a distal end; a cable connecting said imaging module to the connector in said sheath; image processing electronics in said reusable portion that receive image data from the imaging module via said cable and said connectors and produce processed image data; and transmission facilities in said reusable portion configured to transmit said processed image data for display at a physically remote unit.

The endoscope of the immediately preceding paragraph can further include a flexible cap that is configured to initially cover the open end of said sheath and to be manually removed therefrom and placed over the part of the reusable portion that extends distally from the sheath in the assembled endoscope, wherein the reusable portion of the assemble endoscope is entirely covered and protected from the environment by said cap and sheath.

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all such details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 3:
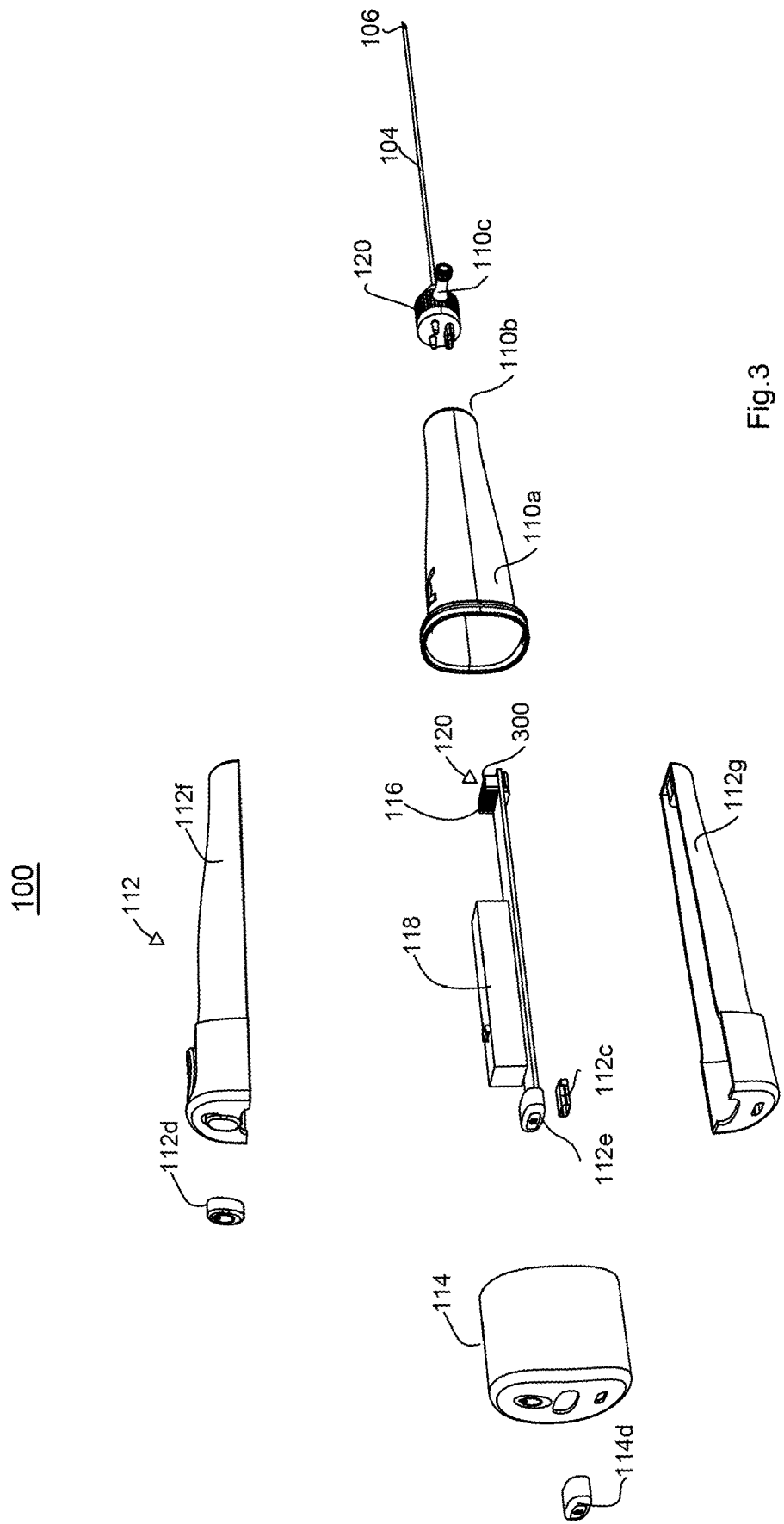
FIG. 3 is another exploded perspective view of an endoscope, according to some embodiments.

FIG. 1 is a perspective view of an endoscope 100 communicating with a remote unit 102 via a cable or wirelessly and FIGS. 2 and 3 are exploded views of endoscope 100, according to some embodiments. Remote unit 102 can be a display screen, a tablet or mobile device with a display, or a camera application program in a computer. Endoscope 100 comprises a single-use portion 108 (FIG. 2) that comprises a needle 104 with an imaging module 106 at its distal end, a funnel-shaped sheath 110 that is open at its proximal end 110a and has a distal end 110b from which needle 104 protrudes distally, and a fluid port 110c that communicates with an internal fluid lumen in needle 104 that terminates in a fluid ports 810, 820 and 830 (FIG. 8) at the distal end of needle 104. Endoscope 100 further comprises a reusable portion 112 (FIG. 2) that contains electronics and other components. Reusable portion 112 has a smaller cross-section distal part 112a that fits in sheath 110 to form the assembled endoscope 100 seen in FIG. 1 and a larger cross-section proximal part 112b that extends proximally of sheath 110 in the assembled endoscope 100 seen in FIG. 1. A cap 114 serves two different functions—before endoscope 100 is assembled, cap 114 is sterile and covers and seals the open end 110a of sheath 110. After the reusable and single-use portions 108 and 112 have been assembled, cover 114 covers and seals from fluids the larger cross-section part 112b of reusable portion 112.

Preferably, single-use portion 110, with cap 114 covering the open end 110a, is sterilized at the point of manufacture, shipped to users in a sterile package, and kept in the pouch until needed for a medical procedure. For use in a medical procedure, the user takes single-use portion 108 out of the sterile package, removes cap 114, inserts smaller cross-section 112a of reusable portion 112 into sheath 110, and places cap 114 over the larger cross-section part 112b of reusable portion 112. Reusable portion 112 communicates with unit 102 via a cable 113 extending from a port 112c at the proximal end of reusable portion 112 to unit 102 (the cable is schematically shown by broken line 113) or wirelessly by WiFi or BLE 5.0, in which case cable 113 is not used. Unit 102 is configured to display images send from endoscope 100 and can include electronics for processing and/or storing the images and/or transmitting the images to other equipment such as a workstation or archival storage. The proximal end of reusable portion 112 preferably includes a manual off-on switch 112d and a manual image control switch 112e that controls image taking with an imaging module at the distal end of needle 104. Cap 114 is made of a soft and pliable material and has flexible portions 114a, 114b, and 114c that align with switches 112d and 112 and with cable oil 112c, respectively, to allow manual operation of the switches through cap 114 and cable access to port 112e when endoscope is assembled as seen in FIG. 1. Cap 114 is open at its distal end.

Notably, as seen in FIG. 1 the only surfaces of endoscope 100 that are exposed to the environment, such as to fluids in a medical procedure, are single use—sheath 110 and needle 104 that form single-use portion 108 and cap 114 that covers and seals the entire part 112b (FIG. 2) of reusable portion 112 that is proximal of sheath 110 when endoscope 100 is assembled. Reusable portion 112 is not exposed at all. When the connection to unit 102 is by cable, the connector to reusable unit 112 tightly fits in an opening 114c (FIG. 2) in cap 114 to keep fluids from reaching reusable unit 112. When a wireless connection is used, the cable connector opening is sealed with a plug 114d (FIG. 3). Thus, very little disinfecting can be required for employing reusable portion 112 in another medical procedure after disposing cap 114 and single-use portion 108 after completing one medical procedure. The assembled scope is entirely sterile.

FIG. 3 illustrates components of endoscope 100 according to some embodiments. Reusable portion 112 comprises a housing made of molded halves 112f and 112g that are snapped or glued to each other in a fluid-tight configuration. This housing encloses a circuit board 116 with image processing electronics, a rechargeable battery 118 powering the electronics on circuit board 116 and imaging module 800 (FIG. 8) at the distal end of needle 104, and electrical connectors 120 to make electrical contact with matching contacts 600a (FIG. 6) in single-use portion 108.

Figure 4:
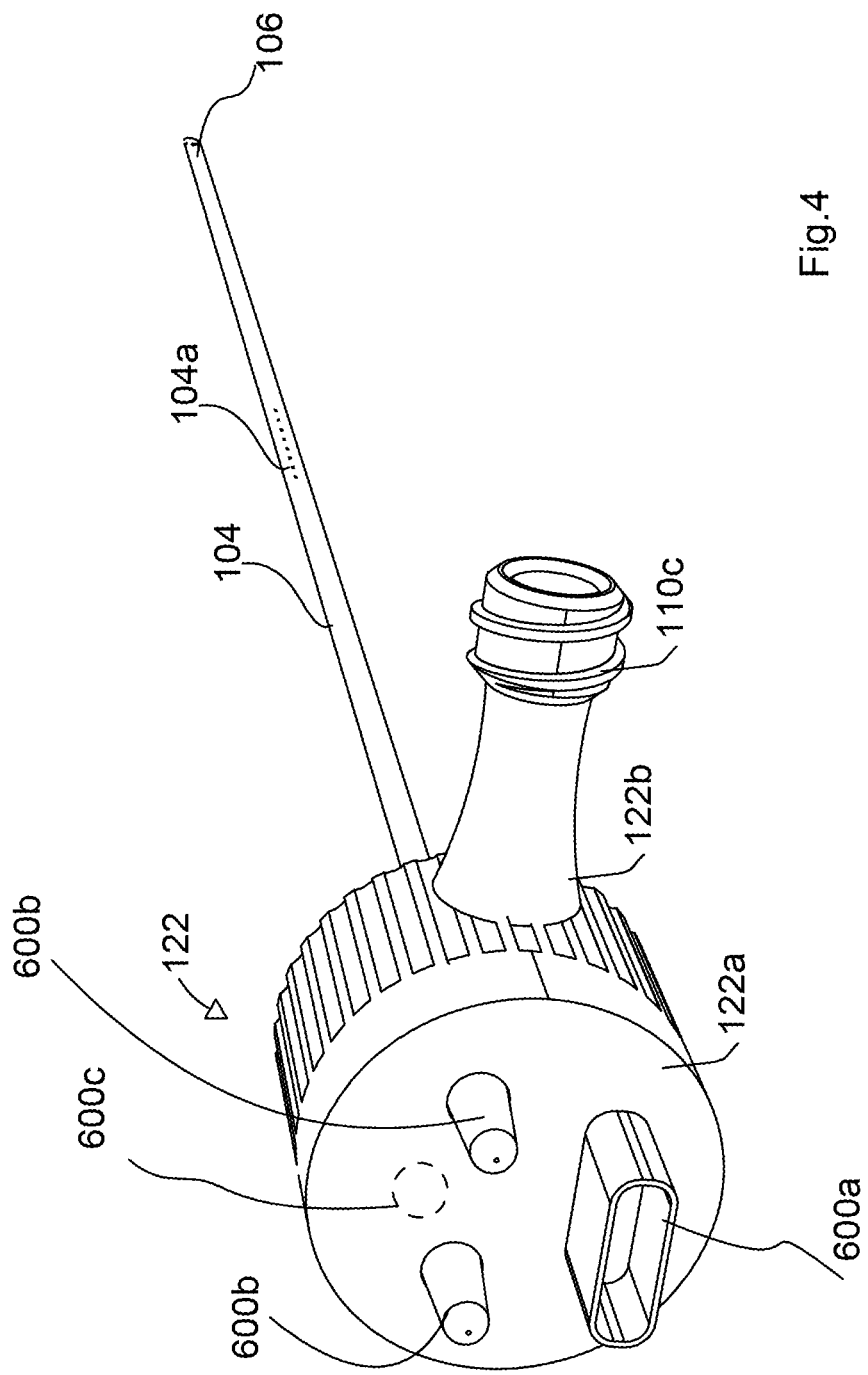
FIG. 4 is a perspective view of a needle housing and a needle, according to some embodiments.
Figure 7:
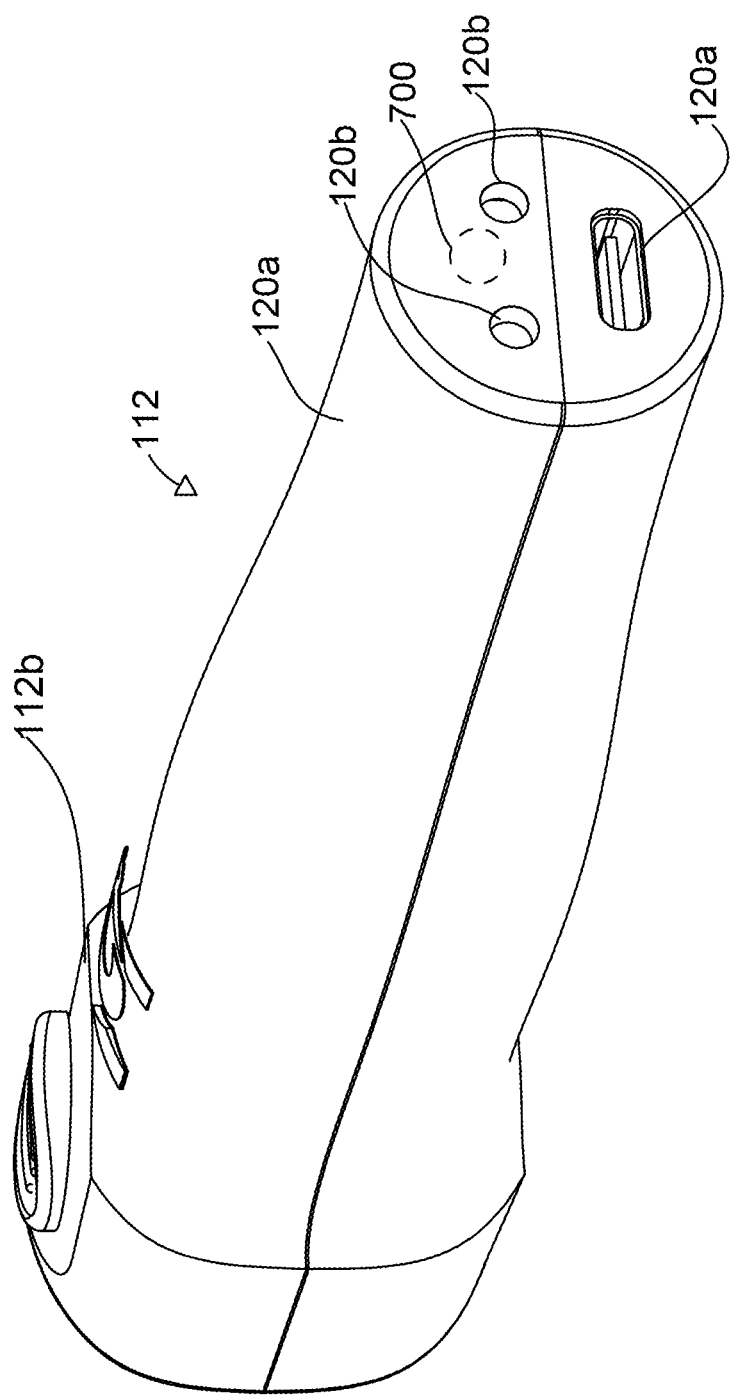
FIG. 7 is a perspective view of a reusable portion of an endoscope, according to some embodiments.

FIG. 4 illustrates needle housing 122 in more detail. Needle housing 122 comprises a cylindrical element 122a that has ribs around its circumference that fit in an opening in the distal end of sheath 110 when housing 122 is forced into and friction-fitted therein in the direction of the arrow between them seen in FIG. 3. Housing 122 has at its proximal end a male contact 600a that meshes with female connector 120a (FIG. 7) at the distal end of reusable portion 112. Registration pins 600b fit in registration openings 120b (FIG. 7) at the distal end of reusable portion 112. Housing 122 further includes a passageway for an electrical cable 806 (FIG. 8) from connector 600a to imaging module 800 that passes inside needle 104.

Figure 5:
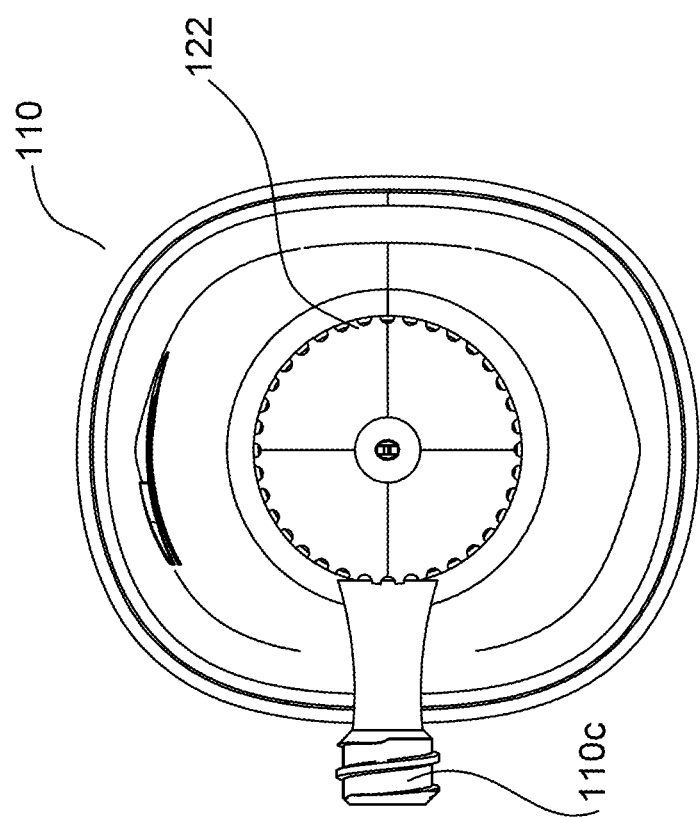
FIG. 5 is a sectional view of a needle housing as fitted in a sheath of an endoscope, according to some embodiments.

FIG. 5 shows a cross section, in a plane transverse to the long axis of needle 104, of housing 122 assembled into the distal end of sheath 110.

Figure 6:
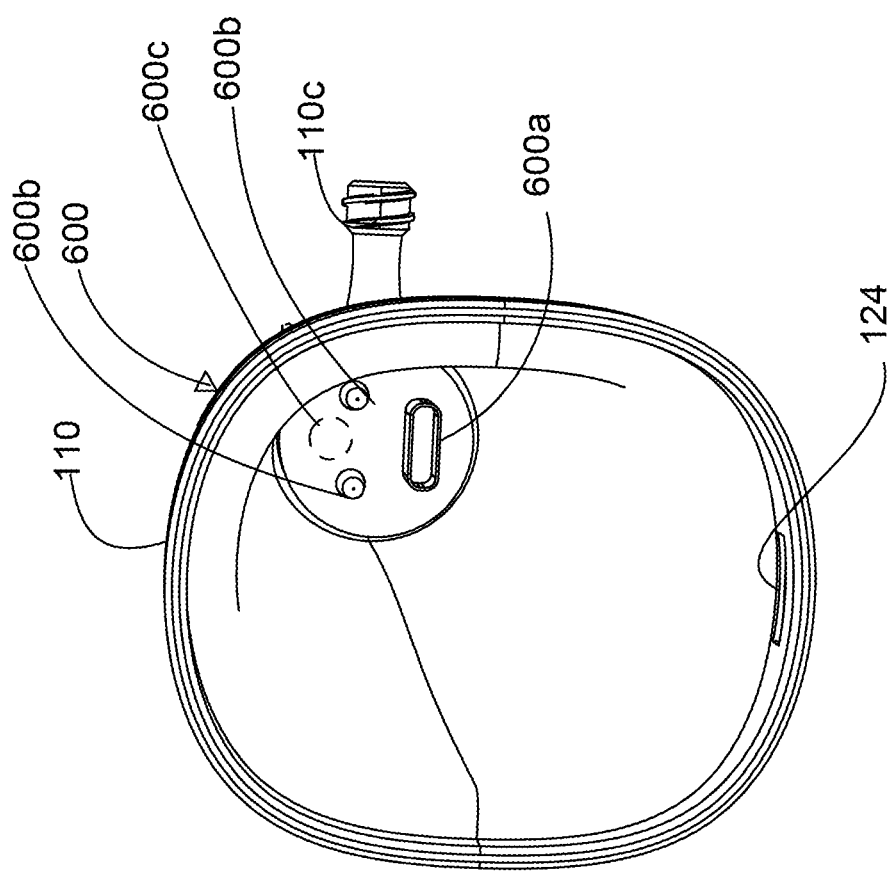
FIG. 6 is a perspective view of an inside of a sheath of an endoscope, according to some embodiments.

FIG. 6 shows in perspective a view into the open proximal end of sheath 110, where connector 600a and registration pins 600b are visible. The ensure that reusable portion 112 is inserted in sheath 110 in proper orientation, a channel 124 (FIG. 6) can be included in the lower part of the inner wall of sheath 110 and a matching rib (not shown) can be included at the lower outer wall of distal portion 112a of reusable portion 112 to ensure that the two portion of the endoscope can only be assembled in the correct way. Alternatively, or in addition, the inner wall of sheath 110 and the outer wall of distal part 112a of reusable portion 112 can be shaped such that reusable portion 112 can go into sheath 110 only in the correct relative orientation—for example, the cross-section of the inner wall of sheath 110 and the outer wall of distal portion 112a or reusable portion 112 can be narrower at one side than at the other. Thus, an effort to place reusable portion 112 into sheath 110 in a wrong mutual orientation will easily show a need to correct that.

FIG. 8a shows in a side view a distal part of needle 104 and FIG. 8b shows that part in perspective. Cable 806 extends from connector 600a (FIGS. 4 and 6) to imaging module 800, which comprises an illumination source 802 such as one or more LEDs and an imaging sensor 804 such as a CMOS sensor. Notably, sensor 804 is mounted in needle 104 such that its imaging plane is tilted relative to the long axis of needle 104, for example at an angle such that the central axis of the direction of view of sensor 804 is at 30 degrees to the long axis of needle 104. Illumination source 802 is likewise tilted to illuminate the field of view of sensor 804. This makes it possible to visualize a larger volume of tissue by rotating needle 104 relative to the tissue being examined. Also notably, the distal end of needle 104 is beveled, to a sharp tip 808 to facilitate puncturing and entering tissue as needed. Distal fluid ports 810, 820 and 830 is provided in needle 104, which communicated with fluid port 110c through a fluid channel 812 formed by space around cable 806 in needle 104. An opening 814 in needle 104 is sealed with an adhesive used on secure imaging module 800 at the distal end of needle 104. In a non-limiting example, needle 104 has an outside diameter of 1-1.6 mm and fluid lumen 812 equivalent to a lumen with an inside diameter greater than 0.55 mm, corresponding to 22 Ga or more.

According to some embodiments, the illumination source in imaging module 800 is not LEDs at the distal end of needle 104 but comprises a preferably more powerful light source 300 with a heat sink (FIG. 3) that can be one or more LEDs inside reusable portion 112. Light from source 300 passes through a light port (not shown) at the distal end or reusable portion 112 and then through a matching light port 600c (FIGS. 4 and 6) in sheath 110 and into a light transmitting channel 104a (schematically shown in FIG. 4) that extends from light port 600c to the distal end of needle 104 and is configures to illuminate the field of view of sensor 804 (FIG. 8). The light channel can be one or more fiber optic strands. Of course, in this case no LEDs 802 are present in imaging module 800. In this embodiment, the manufacturing cost of single-use portion 108 is reduced as it does not include LEDs 802, and the cross-section of needle 104 can be reduced as it does not need to accommodate LEDs 802.

Figure 9:
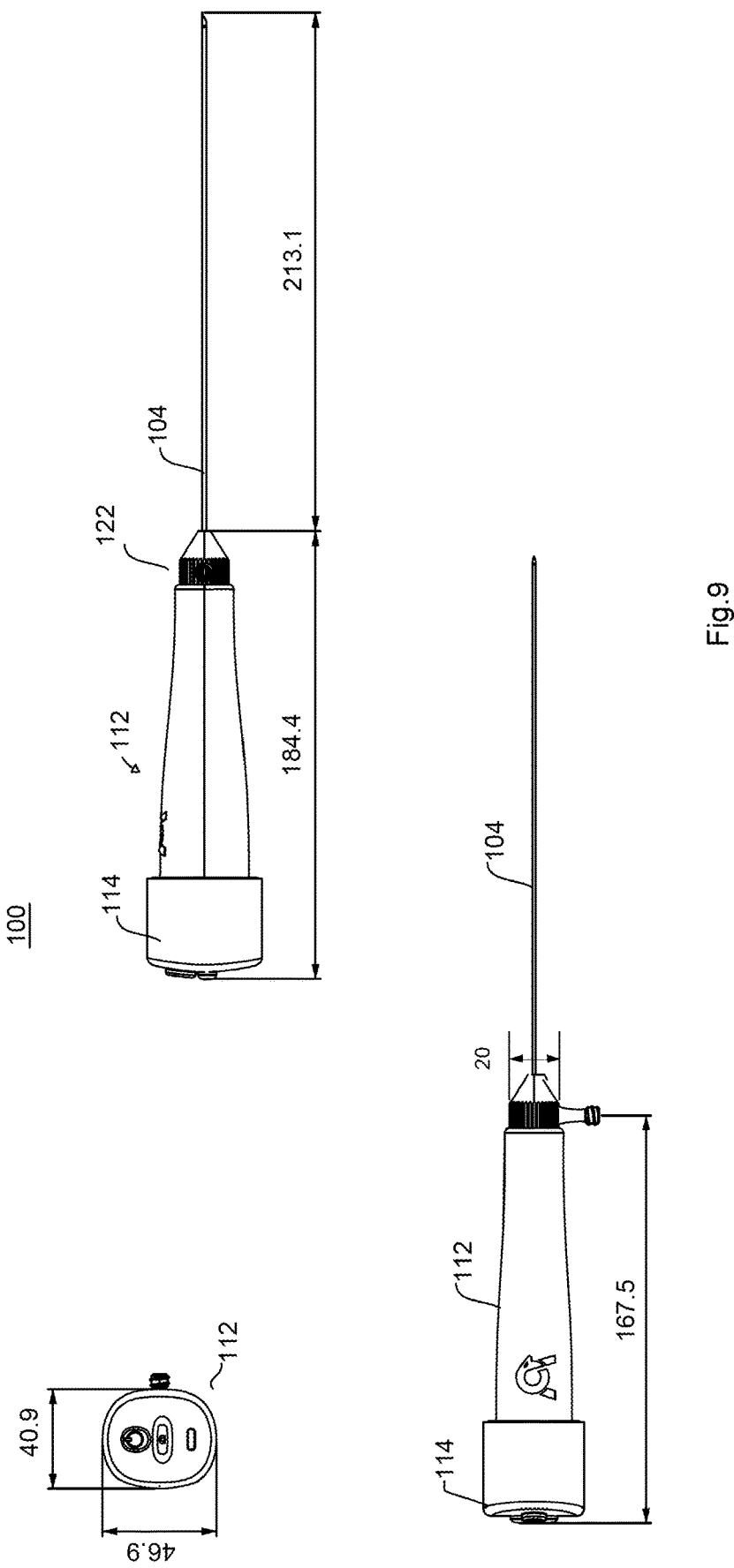
FIG. 9 shows non-limiting example of dimensions of an endoscope, according to some embodiments.

FIG. 9 shows a non-limiting example of dimensions in mm of endoscope 100. At upper left, the outer dimensions of the proximal end of reusable portion 112 are 40.9 and 46.9 mm, the length of reusable portion 112, with cap 114 on and housing 122 is 184 mm, the length of needle 104 is 213.1 mm, and the distance from the proximal end of reusable portion 112 with cap 114 on, to the center of fluid port 110c is 167.5 mm.

FIGS. 10a-d show in perspective distal tips that fits at the distal end of needle 104 according to some embodiments. FIG. 10a shows an example that has a space 1001 for a sensor 804 (FIG. 8), windows 1002 for light illumination, which can be for light conductors (fiber optic strands) or an LED mounted in window 1004, and a distal fluid port 1004. FIG. 10b shows a different configuration, with space 1006 for a sensor 800, windows 1008 for optical channels, and a distal port 1010. FIG. 10c show a configuration with space 1012 for sensor 800, windows 1014 for light conductors, and distal fluid port 1016. FIG. 10d shows a space 1018 for a sensor 800, and a distal fluid port 1020; illumination can be provided by LEDs (not shown) above sensor 800 or a light conductor window (not shown) above sensor 800. Note that the distal end of the tip in each of FIGS. 10a and 10b is oval and has a distal surface in a plane angled relative to the long axis of needle 104 while the distal end of each tip in FIGS. 10c and 10d can be circular.

Endoscope 100 can be used for different medical procedures. One example is Arthroscopic surgery or arthroscopy, which is a minimally invasive orthopedic procedure to diagnose and treat joint problems. Such procedures can use endoscope 100 and specialized surgical tools to access a joint through tiny, keyhole incisions. Other nonlimiting examples include providing access to visualize and treat other tissue in a patient such as breast and other soft tissue and bone structures.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

The invention claimed is:

1. An endoscope (100) comprising:
   a single-use portion (108) that comprises:
   (a) an elongated, hollow, funnel-shaped sheath (110) that has an open proximal end and an open distal end, is entirely made of plastic material, and is free of electrical or electronic contacts or mechanical actuators, and
   (b) a needle housing (122) that has a proximal end fitted at the open distal end of the sheath and a needle (104) that extends distally from a distal end of the needle housing and has an imaging module (106) at a distal end;
   a reusable portion (112) that comprises a proximal part (112b) and an elongated distal part (112a), wherein said distal part of the reusable portion is configured to be removably inserted by hand distally into said sheath through said open proximal end thereof to thereby form, together with the single-use portion, an assembled endoscope, with said distal part of the reusable portion entirely inside and covered by the sheath and said proximal portion of the reusable portion extending proximally from the sheath and remaining not covered by any component physically connected to the sheath;
   a first connector (600a) secured at the proximal end of the needle housing and electrically coupled with said imaging module and a second connector (120a) at said distal part of the reusable portion, wherein said connectors are configured to electrically couple in the assembled endoscope; and
   wherein said reusable portion comprises a circuit board (116) with imaging electronics configured to communicate with the imaging module through said first and second connectors in the assembled endoscope, including for processing image data acquired with said imaging module and to send image data for remote display at a unit physically uncoupled with the endoscope.

2. The endoscope of claim 1, including a sterile cap made of soft and pliable material that releasably seals said open end of the sheath before the single-use and reusable portions are assembled to form the endoscope and is configured for removal by hand for complete detachment from the sheath prior to insertion of the reusable portion into the sheath to form the assembled endoscope.

3. The endoscope of claim 1, including a cap made of soft and pliable material that releasably covers and seals said proximal portion of the reusable portion and a proximal end of the sheath in the assembled endoscope and wherein the sheath covers the entirety of the reusable portion that is distal from the proximal portion covered by the cap when the endoscope is assembled, so that the reusable portion is not exposed to the environment during a medical procedure.

4. The endoscope of claim 3, in which the proximal end of the reusable portion has one or more manually operated switches and said cap is configured to securely fit over said one or more switches and seal them from external fluids in the assembled endoscope while allowing manual operation of the one or more switches through the cap.

5. The endoscope of claim 1, including a sterile cap made of soft and pliable material that releasably seals said proximal end of the sheath before the single-use and reusable portions are assembled to form the endoscope, wherein said cap is configured to securely fit thereafter over the proximal part of said reusable unit to seal it from external fluids and the entirety of the reusable portion that is distal from the proximal end thereof is within said sheath in the assembled endoscope.

6. The endoscope of claim 1, in which the imaging module at the distal end of the needle comprises a video sensor with a direction of view that has a central axis angled relative to a long axis of the needle and one or more LEDs configured to illuminate a field of view of said sensor.

7. The endoscope of claim 1, in which the imaging module at the distal end of the needle comprises a video sensor with a direction of view that has a central axis angled 30 degrees relative to a long axis of the needle and one or more LEDs configured to illuminate a field of view of said camera.

8. The endoscope of claim 1, in which the imaging module at the distal end of the needle comprises a video sensor with a field of view that has a central axis angled relative to a long axis of the needle, the reusable portion includes an LED-implemented light source, the single-use portion includes a light port and one or more light conductors from the light port to the distal end of the needle, and the reusable portion includes a light port coupling with the light port of the single-use portion to transmit light from the light source in the reusable portion to the distal end of the needle to illuminate a field of view of the sensor.

9. The endoscope of claim 1, in which the reusable portion includes a battery, an LED light source powered with the battery, and a heat sink for the light source.

10. The endoscope of claim 1, in which said single-use portion includes a first fluid port at a distal portion of the sheath, and said needle includes a second fluid port at a distal end thereof, and said single-use portion includes an internal lumen coupling said first and second ports for fluid flow.

11. The endoscope of claim 1, in which said needle has an outside diameter of 1-1.6 mm and includes a fluid lumen with an inside dimension equivalent to a diameter greater than 0.55 mm and matching 22 Ga or more.

12. The endoscope of claim 1, in which the distal end of the needle is beveled and has a sharp tip to facilitate puncturing and penetrating tissue.

13. The endoscope of claim 1, in which said imaging module comprises a video sensor with an imaging plane angled at 20-80 degrees to a longitudinal axis of the needle to thereby provide a central direction of view of the camera that is angled relative to said axis.

14. The endoscope of claim 1, in which said reusable portion includes a transmitter configured to wirelessly transmit image data to a remote display.

15. The endoscope of claim 1, in which said reusable portion includes a port for a cable configured to transmit image data to a remote display.

16. An endoscope comprising:
a single-use portion that includes a funnel-shaped sheath with an open proximal end, a needle housing at a distal end of the sheath, and a needle that extends distally from a distal end of the needle housing;
a reusable portion that includes a proximal part and a distal part that extends distally from the proximal part and releasably fits by hand in the sheath to thereby form, together with the sheath, the needle housing, and the needle, an assembled endoscope in which the proximal part of the reusable portion extends proximally from the sheath and the entirety of the distal part of the reusable portion is covered by and is within the sheath;
electrical connectors at a distal end of the reusable portion and at a proximal portion of the needle housing that make electrical contact with each other in the assembled endoscope;
said needle further comprising an imaging module at a distal end thereof;
a cable connecting said imaging module to the electrical connectors at the proximal portion of the needle housing;
image processing electronics in said reusable portion that receive image data from the imaging module via said cable and said connectors and produce processed image data; and
a flexible cap made of soft and pliable material that is configured to initially cover the open end of said sheath before the distal part of the reusable portion is inserted therein and to be manually removed therefrom in its entirety and thereafter is placed over the part of the reusable portion that extends proximally from the sheath in the assembled endoscope, wherein the reusable portion and a proximal portion of the sheath in the assembled endoscope are entirely covered and protected by said cap and sheath.

17. The endoscope of claim 16, in which the sheath and the reusable portion are configured with a channel and a rib interacting to restrict the sheath and reusable portion to a fit in only one orientation relative to each other.

18. An endoscope comprising:
a single-use portion that includes a funnel-shaped sheath with an open proximal end, wherein the sheath is free of electrical contacts, and a needle portion that extends distally from the sheath and has an imaging module at a distal end;
a reusable portion that includes a proximal part and a distal part that extends distally from the proximal part and which releasably inserts by hand in the sheath to form an assembled endoscope, with the proximal part of the reusable portion extending proximally from the sheath and the distal part of the reusable portion entirely covered by the sheath in the assembled endoscope;
electrical connectors at a distal end of the reusable portion and the at a proximal end of the needle portion that make electrical contact with each other in the assembled endoscope;
a cable connecting said imaging module to the electrical connectors at the proximal end of the needle portion;
image processing electronics in said reusable portion that receive image data from the imaging module via said cable and said connectors and produce processed image data; and
a disposable cap made of soft and pliable material that is free of a permanent physical connection to the sheath and removably fits over the proximal part of the sheath before the reusable portion is inserted therein and thereafter fits over the reusable portion that extends proximally from the sheath and over a proximal end of the sheath, wherein the reusable portion and said proximal end of the sheath are entirely covered and protected by said cap and sheath in the assembled endoscope and wherein the cap is configured for removal in in its entirety from the sheath and reusable portion by hand.

* * * * *